(12) United States Patent
Wang et al.

(10) Patent No.: US 7,704,719 B2
(45) Date of Patent: Apr. 27, 2010

(54) GLUCOSE ISOMERASE MUTANTS, DNA THEREOF AND USE THEREOF

(75) Inventors: Jun Wang, Hong Kong (CN); Caike Jin, Hong Kong (CN); Rongzhao Fu, Hong Kong (CN); Dong Shen, Hong Kong (CN)

(73) Assignee: GeneHarbor (HK) Technologies Ltd., Hong Kong (CN)

( * ) Notice: Subject to any disclaimer, the term of this patent is extended or adjusted under 35 U.S.C. 154(b) by 0 days.

(21) Appl. No.: 12/093,859

(22) PCT Filed: Oct. 30, 2006

(86) PCT No.: PCT/CN2006/002901

§ 371 (c)(1),
(2), (4) Date: Aug. 13, 2008

(87) PCT Pub. No.: WO2007/056930

PCT Pub. Date: May 24, 2007

(65) Prior Publication Data

US 2008/0305529 A1 Dec. 11, 2008

(30) Foreign Application Priority Data

Nov. 18, 2005 (CN) .................. 2005 1 0123606

(51) Int. Cl.
*C12N 9/00* (2006.01)
*C12N 9/92* (2006.01)
*C12N 1/20* (2006.01)
*C12N 15/00* (2006.01)
*C07H 21/04* (2006.01)

(52) U.S. Cl. .............. 435/234; 435/183; 435/252.3; 435/320.1; 536/23.2

(58) Field of Classification Search .............. None
See application file for complete search history.

(56) References Cited

U.S. PATENT DOCUMENTS

| 5,656,497 A | 8/1997 | Zeikus et al. |
| 2008/0113415 A1 | 5/2008 | Wang et al. |

FOREIGN PATENT DOCUMENTS

| CN | 1213003 | 4/1999 |
| CN | 1693473 | 11/2005 |
| CN | 1693476 A | 11/2005 |
| CN | 1743454 | 3/2006 |
| CN | 1702172 | 11/2008 |
| EP | 0351029 | 1/1990 |
| EP | 1264883 | 12/2002 |
| JP | 2000333684 | 12/2000 |
| WO | 2005116217 A1 | 12/2005 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Ge et al., "Immobilization of Glucose Isomerase and Its Application in Continuous Production of High Fructose Syrup", Applied Biochemistry and Biotechnology, 1998, pp. 17-29, vol. 69.
Kaneko et al., "Characterization of Acid-Stable Glucose Isomerase from *Streptomyces* sp., and Dedvelopment of Single-Step Processes for High-Fructose Corn Sweetener (HFCS) Production", Biosci. Biotechnol. Biochem. 2000, pp. 940-947, vol. 64(5).
Lee et al., "Cloning, Sequencing and Biochemical Characterization of Xylose Isomerase from *Thermoanaerobacterium saccharolyticum* Strain B6A-RI", J. of General Microbiology, 1993, pp. 1227-1234, vol. 139.
Vieille et al., "Xylose Isomerases from Thermotoga", Methods in Enzymology, 2001, pp. 215-224, vol. 330.
Lee et al., "Genetic Organization Sequence and Biochemical Characterization of Recombinant B-xylosidase from *Thermoanaerobacterium saccharolyticum* strain B6A-RI", J. of General Microbiology, 1993, pp. 1235-1243, vol. 139.
Sriprapundh et al., "Molecular Determinants of Xylose Isomerase Thermal Stability and Activity: Analysis of Thermozymes by Site-Directed Mutagenesis", Protein Engineering, 2000, pp. 259-265, vol. 13(4).
Sriprapundh et al., Directed Evolution of *Thermotoga neapolitana* Xylose Isomerase: High Activity on Glucose at Low Temperature and Low pH, Protein Engineering, 2003, pp. 683-690, vol. 16(9).
IUPAC-IUB Joint Commission on Biochemical Nomenclature (JCBN), "Nomenclature and Symbolism for Amino Acids and Peptides", Eur. J. Biochem., 1984, pp. 9-37, vol. 138.

(Continued)

*Primary Examiner*—Christian L Fronda
(74) *Attorney, Agent, or Firm*—The Webb Law Firm

(57) ABSTRACT

This invention provides a series of recombinant *Thermoanaerobacterium saccharolyticum* glucose isomerases with improved catalytic activity and thermostability obtained by using recombinant techniques. These recombinant glucose isomerases comprise amino acid variation including phenylalanine (Phe) at position 139, alanine (Ala) at position 182, serine (Ser) at position 187, and glutamine (Gln) at position 299, and carry at least one additional mutated amino acid at position 87, position 217, position 260 or position 276, and possess a higher catalytic activity than that of the wild-type when using D-glucose as substrate. These recombinant glucose isomerases can be used for direct production of high fructose corn syrup containing 55.% [wt] or higher concentration of fructose.

6 Claims, 1 Drawing Sheet

OTHER PUBLICATIONS

Ho et al., "Site-Directed Mutagenesis by Overlap Extension Using the Polymerase Chain Reaction", Gene, 1989, pp. 51-59, vol. 77.

White, "PCR Protocols: Current Methods and Applications", Methods in Molecular Biology, 1993, pp. 277-286, vol. 15.

Dische et al., "A New Spectrophotometric Method for the Detection and Determination of Keto Sugars and Trioses", 1951, pp. 583-587, vol. 192.

Nakamura, "Determination of Fructose in the Presence of a Large Excess of Glucose—Part V—A Modified Cysteine-Carbazole Reaction", Agr. Biol. Chem., 1968, pp. 701-706, vol. 32(6).

Bhosale et al.; "Molecular and Industrial Aspects of Glucose Isomerase"; Microbiological Reviews, American Society for Microbiology, Jun. 1, 1996; pp. 280-300; vol. 60, No. 2; XP009008737; Washington, DC, US.

* cited by examiner

GLUCOSE ISOMERASE MUTANTS, DNA THEREOF AND USE THEREOF

FIELD OF THE INVENTION

The present invention relates to molecular biology and biotechnology, and specifically relates to recombinant glucose isomerases with improved activity or both of improved activity and thermostability, the method of preparing the same using recombinant techniques, and use of the same.

BACKGROUND OF THE INVENTION

Glucose isomerase (E.C.5.3, 1.5, or xylose isomerase) is a key enzyme in the pentose phosphate pathway. It is one of the most important industrial enzymes (Kaneko et al., *Bioscience, Biotechnology, and Biochemistry* 2000, 64:940-947). In the food industry, it is used for the manufacture of high fructose corn syrup.

The equilibrium of the isomerization of D-glucose to fructose is primarily dictated by the temperature of the reaction. The higher the temperature, the more the fructose in the final reaction mixture. At present, the commercial glucose isomerases come mainly from *Actinoplanes missouriensis, Bacillus coagulans* or *Streptomyces* species, and are not stable at high temperature (e.g. temperature above 65° C.). Consequently, the current commercial isomerization is restricted to operate at around 60° C. and the products normally contain no more than 44% of fructose. The high fructose corn syrup containing higher fructose is therefore generated using expensive chromatographic enrichment, leading to higher production cost.

Scientists around the world have been working on the identification of thermostable and highly active glucose isomerases from thermophilic bacteria, and production of the same via protein engineering. J. G. Zeikus and his collaborators isolated and studied thermostable glucose isomerases from thermophilic bacteria, such as *Thermoanaerobacterium saccharolyticum* (hereinafter referred to as *T. saccharolyticum*) and *Thermotoga neapolitana* (Lee et al., *Journal of General Microbiology*, 139:1227-1234, 1993; Vieille et al., *Methods in Enzymology*, 330:215-24, 2001; Lee et al., *Journal of General Microbiology*, 139:1241-1243, 1993; Scriprapundh et al., *Protein Engineering*, 13:259-265, 2000; Scriprapundh et al., *Protein Engineering*, 16:683-690, 2003; Zeikus et al., U.S. Pat. No. 5,656,497). Nevertheless, the thermostabilities of the thermostable glucose isomerases from these or other bio-resources are still much to be desired, as the activities of thereof are low, and thus are not applicable to industrial applications. Therefore, glucose isomerase with high activity, or high activity and thermostability remains desirable.

SUMMARY OF THE INVENTION

By using genetic and protein engineering of *Thermoanaerobacterium saccharolyticum* glucose isomerase, this invention provides a series of glucose isomerases with improved catalytic activity suitable for the production of high fructose corn syrup containing high concentration of fructose.

The objective of the present invention is to provide highly active glucose isomerase mutants. Another objective of the invention is to use the glucose isomerase mutants to directly produce high fructose corn syrup containing 55% or higher concentration of fructose. Still another objective of the invention is to use the glucose isomerase mutants to produce high fructose corn syrup containing less than 55% fructose.

In order to achieve the above-mentioned objects, the inventors of the present invention have conducted extensive experiments. The inventors of the present invention have introduced mutations, by site-directed mutagenesis, into the *T. saccharolyticum* glucose isomerase gene and obtained a series of highly active or highly active and thermostable glucose isomerase mutants after screening on MacConkey agar. More specifically, the molecular biotechniques being used to generate glucose isomerase mutants include, construction of plasmid carrying the wild-type glucose isomerase gene; design of mutation sites and the amino acids after mutations; design of appropriate primers; PCR amplification of DNA fragments using the wild-type glucose isomerase gene as template; assembly of the DNA fragments; PCR amplification of the full-length glucose isomerase genes containing the mutation(s); cloning of the mutant genes into appropriate vectors; transformation of the vectors containing the genes into appropriate host cells; screening of the transformants for clones carrying desired glucose isomerase mutants; isolation of the plasmid DNA from the positive clones; and carrying out DNA sequencing to verify the mutations. Finally, the activity of the mutated isomerase is assessed using D-glucose as substrate, and mutated isomerase according to the present invention with higher catalytic activity than that of the wild-type is selected.

For the preparation of the novel glucose isomerases in this invention, suitable vectors include but are not limited to prokaryotic expression vectors pGEMT-Easy, pRSET and pET21; include but are not limited to eukaryotic expression vectors pYD1 and pYES2/GS; include but are not limited to cloning vectors pUC18/19 and pBluescript-SK.

For the preparation of the glucose isomerase mutants in this invention, the mutated glucose isomerase gene can be expressed intra-cellularly in prokaryotic or eukaryotic cells, or can be expressed extra-cellularly in prokaryotic or eukaryotic cells by using any other techniques known in the art.

For the preparation of the novel glucose isomerases in this invention, the host cells can be prokaryotic or eukaryotic cells. The prokaryotic cells include but are not limited to *E. coli, Bacillus subtilis, Bacillus brevis, Bacillus megaterium* (e.g. *B. megaterium* BP931), *T. saccharolyticum* and *Streptomyces* (e.g. *S. diastaticus* M1033). The eukaryotic cells include but are not limited to *Saccharomyces cerevisiae* and *Pichia pastoris* (egg. *P. pastoris* GS115/9891).

The glucose isomerase mutant according to this invention, using Sequence 2 in the Sequence Listing as the reference sequence, comprises amino acid mutations including phenylalanine (Phe) at position 139, alanine (Ala) at position 182, serine (Ser) at position 187, and glutamine (Gln) at position 299, as well as at least one mutation at position 87, position 217, position 260, or position 276, and using D-glucose as substrate, possesses higher catalytic activity than the wild-type. Preferably, the amino acid at the position 87 is methionine (Met) or leucine (Leu); the amino acid at the position 217 is arginine (Arg), or tryptophan (Trp) or glycine (Gly); the amino acid at the position 260 is glutamic acid (Glu) or alanine (Ala); and/or the amino acid at the position 276 is glycine (Gly) or threonine (Thr). Sequence ID: NO.4 in the Sequence Listing shows the amino acid sequence of a glucose isomerase mutant according to this invention, where Xaa represents the mutated amino acid. The glucose isomerase mutants according to this invention include the amino acid sequences of MGI4-F87L, MGI4-F87M, MGI4-V217R, MGI4-V217W, MGI4-D260E, MGI4-F276G, MGI4-24, MGI4-25, MGI4-34 and MGI4-35 as shown in Table 2.

These glucose isomerase mutants possess high catalytic activity. For example, in a series of glucose isomerase mutants obtained according to this invention, a seven-mutation mutant MGI4-34 possesses a specific activity 769% higher than that of wild-type and still has 50% or more of the original activity after heat treatment at 80° C. for 26 hours. Another seven-mutation mutant MGI4-35 possesses a specific activity 727% higher than that of wild-type, and still has 50% or more of the original activity after heat treatment at 80° C. for 27 hours.

The glucose isomerase mutants with high catalytic activity or high catalytic activity and thermostability obtained according to this invention can be used for direct production of high fructose corn syrup containing 55 wt. % or higher concentration of fructose, or for the production of high fructose corn syrup containing less than 55 wt. % fructose. The described glucose isomerase mutant can be used for the production of crystallized fructose with fructose content of 90 wt. % or higher.

The glucose isomerase mutants can be used in an unpurified crude enzyme form, or in partially purified enzyme form, or as completely purified enzyme preparation. If required, the glucose isomerase mutants can be prepared as immobilized enzyme, or immobilized cells using known immobilization methodologies.

DEFINITIONS

Term "wild-type" as used herein refers to the glucose isomerase from *Thermoanaerobacterium saccharolyticum* ATCC 49915, with its DNA sequence as Sequence 1 in the Sequence Listing, with its amino acid sequence as Sequence 2 in the Sequence Listing. The DNA sequence of the wild-type glucose isomerase in this invention is different in two nucleotides from the published DNA sequence of glucose isomerase from the same species (Lee et al., *Journal of General Microbiology*, 139:1227-1234, 1993; GenBank L09699); namely, the nucleotides of the wild-type glucose isomerase in this invention at position 241-242 are GC, coding alanine (Ala) at position 81; while the corresponding nucleotides in GenBank L09699 are CG, coding arginine (Arg) at position 81.

Term "reference sequence" as used herein refers to Sequence 1 in The Sequence Listing when it is a DNA sequence; or Sequence 2 in The Sequence Listing when it is an amino acid sequence. The alignment of the reference sequence and the sequences of the glucose isomerase mutants can be done manually or by computer (e.g. using computer softwares CLUSTALW, AMAS, DIALIGN, etc.).

Term "position" or "position x", where x is a numeral, as used herein refers to the position of the nucleotide or amino acid of the mutant sequence in the corresponding reference sequence when the alignment between the glucose isomerase mutants of the present invention and the wild-type glucose isomerase reaches maximum in homology.

Term "glucose isomerase mutant" as used herein refers to an enzyme that using Sequence 2 in the Sequence Listing as the reference sequence, comprises the following mutations: phenylalanine (Phe) at position 139, alanine (Ala) at position 182, serine (Ser) at position 187, and glutamine (Gln) at position 299, and contains at least one mutation at position 87, position 217, position 260, or position 276, and has a catalytic activity higher than that of wild-type glucose isomerase in the reaction of fructose generation using D-glucose as substrate. Therefore, in the present invention, the mentioned glucose isomerase mutants include mutants with an amino acid sequence that is the same as Sequence 4 in the Sequence Listing, or is a conservative substitution of Sequence 4, or is Sequence 4 with addition or deletion of one or several amino acids, or is Sequence 4 with amino terminal or carboxyl terminal deletion, or comprises partial or complete repetition of Sequence 4.

IUPAC nomenclature and symbolism for amino acid abbreviations are used in the present invention (*European Journal of Biochemistry*, 138:9-37, 1984).

DESCRIPTION OF THE PREFERRED EMBODIMENT

Figure 1:
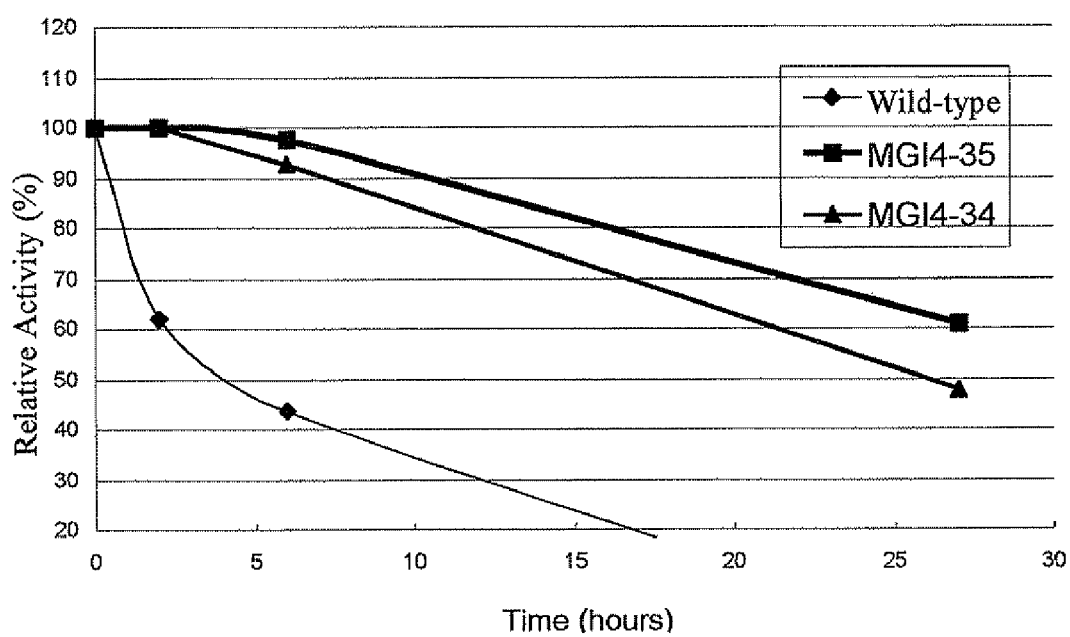
FIG. 1 shows the thermal stability of the wild-type glucose isomerase and glucose isomerase mutants MGI4-34 and MGI4-35 containing seven mutations, at 80° C. Details are described in Example 12.

The examples presented below are for illustration of the invention only and are not intended to be regarded as the limitation of the invention. In the following examples, conventional practice or manufacturers' suggestion/protocol was followed in cases where the conditions were not specified.

Example 1

Amplification of Wild-Type Glucose Isomerase and Construction of pGEMT-TS

Primers T1 and T2 (Table 1) were designed based on the sequence of GenBank L09699 and used to amplify the wild-type glucose isomerase gene from *T. saccharolyticum* ATCC 49915 (ATCC, USA).

The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1, 400 nM primer T2, 1.5 U Taq DNA polymerase (Promega, USA), a loopful of *T. saccharolyticum* colony, and the total volume was adjusted to 50 µl with sterile distilled water.

The PCR amplification program for the reaction was: 95° C., 3 min; then 40 cycles of 95° C., 50 sec, 50° C., 30 sec, 72° C., 1 min; and finally 72° C., 10 min. The amplified PCR product, about 1.5 kb in length, was ligated into vector pGEMT-Easy to generate pGEMT-TS. The pGEMT-TS was sequenced to determine the DNA sequence of the wild-type glucose isomerase as Sequence 1 in the Sequence Listing and the corresponding amino acid sequence as Sequence 2 in the Sequence Listing. The DNA sequence of the wild-type glucose isomerase is different from that of the published DNA sequence of a glucose isomerase from the same species (GenBank L09699) where the nucleotides of the wild-type glucose isomerase in this invention at position 241-242 are GC, coding alanine (Ala) at the amino acid position 81; while the corresponding nucleotides in GenBank L09699 are CG, coding arginine (Arg) at the amino acid position 81.

Example 2

Site-Directed Mutagenesis of Trp139 of Wild-Type Glucose Isomerase

The site directed mutagenesis was done as described by Ho et al., *Gene* 77:51-59, 1989 and White et al., *PCR protocol: current methods and applications*. Totowa, N.J.: Humana Press 1993.

With pGEMT-TS (Example 1) as template, the Trp (W) at position 139 of the wild-type glucose isomerase was mutated to Phe (F) to generate glucose isomerase mutant MGI-W139F by PCR amplification using primers 139FF and 139FR (Table 1) and universal primers T1 and T2 (Example 1).

Fragment T1FR was amplified using primer pair T1 and 139FR. Fragment FFT2 was amplified using primer pair 139FF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 139FR (for fragment T1FR) or 400 nM primer T2 and 400 nM primer 139FF (for fragment FFT2), 1.5 U Pfu DNA polymerase (Promega, USA), 20 ng pGEMT-TS, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1FR and fragment FFT2, were separated on 1% agarose gel and recovered using QIAquick Gel Extraction Kit (QIAGEN, German). The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1FR and 20 ng fragment FFT2, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-W139F was separated on 1% agarose gel and recovered using QIAquick Gel Extraction Kit. Plasmid pGEMT-MG-W139F, generated after ligation of MGI-W139F into pGEMT-Easy, was transformed into competent E. coli HB101 and the transformants were screened for glucose isomerase activity on 1% MacConkey plates containing 1% D-xylose and 50 mg/l ampicillin. Plasmid pGEMT-MGI-W139F DNA was then isolated from the positive clones and sequenced.

Example 3

Site-Directed Mutagenesis of Arg182 of Glucose Isomerase

The site directed mutagenesis was done as described by Ho et al., *Gene* 77:51-59, 1989 and White et al., *PCR protocol: current methods and applications*. Totowa, N.J.: Humana Press 1993.

Using pGEMT-TS (Example 1) as template, the Arg (R) at position 182 of the wild-type glucose isomerase was mutated to Ala (A) to generate glucose isomerase mutant MGI-R182A by PCR amplification with site-directed primers 182AF and 182AR (Table 1) and universal primers T1 and T2 (Example 1).

Fragment T1AR was amplified using primer pair T1 and 182AR. Fragment AFT2 was amplified using primer pair 182AF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 182AR or 400 nM primer T2 and 400 nM primer 182AF, 1.5 U Pfu DNA polymerase, 20 ng pGEMT-TS, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1AR and fragment AFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1AR and 20 ng fragment AFT2, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-R182A was separated on 1% agarose gel and recovered using QIAquick Gel Extraction Kit. Plasmid pGEMT-MGI-R182A, generated after ligation of MGI-R182A into vector pGEMT-Easy, was transformed into competent E. coli HB101 and the transformants were screened for glucose isomerase activity on 1% MacConkey plates containing 1% D-xylose and 50 mg/l ampicillin. Plasmid pGE-MT-MGT-R182A DNA was then isolated from the positive clones and sequenced.

Example 4

Site-Directed Mutagenesis of Phe 187 of Glucose Isomerase

The site directed mutagenesis was done as described by Ho et al., *Gene* 77:51-59, 1989 and White et al., *PCR protocol: current methods and applications*. Totowa, N.J.: Humana Press 1993.

Using pGEMT-TS (Example 1) as template, the Phe (F) at position 187 of the wild-type glucose isomerase was mutated to Ser (S) to generate glucose isomerase mutant MGI-F187S by PCR amplification with site-directed primers 187SF and 187SR (Table 1) and universal primers T1 and T2 (Example 1).

Fragment T1SR was amplified using primer pair T1 and 187SR. Fragment SFT2 was amplified using primer pair 187SF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 187SR or 400 nM primer T2 and 400 mM primer 187SF, 1.5 U Pfu DNA polymerase, 20 ng pGEMT-TS, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1SR and fragment SFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1SR and 20 ng fragment SFT2, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-F187S was separated on 1% agarose gel and recovered using QIAquick Gel Extraction Kit. Plasmid pGEMT-MGI-F187S, generated after ligation of MGI-F187S into vector pGEMT-Easy, was transformed into competent E. coli HB101 and the transformants were screened for glucose isomerase activity on 1% MacConkey plates containing 1% D-xylose and 50 mg/L ampicillin. Plasmid pGEMT-MGI-F187S DNA was then isolated from the positive clones and sequenced.

Example 5

Site-Directed Mutagenesis of Thr299 of Glucose Isomerase

The site directed mutagenesis was done as described by Ho et al., *Gene* 77:51-59, 1989 and White et al., *PCR protocol: current methods and applications*. Totowa, N.J.: Humana Press 1993.

Using pGEMT-TS (Example 1) as template, the Thr (T) at position 299 of the wild-type glucose isomerase was mutated to Gln (Q) to generate glucose isomerase mutant MGI-T299Q by PCR amplification with site-directed primers 299QF and 299QR (Table 1) and universal primers T1 and T2 (Table 1).

Fragment T1QR was amplified using primer pair T1 and 299QR. Fragment QFT2 was amplified using primer pair 299QF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer T1 and 400 nM primer 299QR or 400 nM primer T2 and 400 nM primer 299QF, 1.5 U Pfu DNA polymerase, 20 ng pGEMT-TS, and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1QR and fragment QFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 M dTTP, 50 μM dCTP, 50 μM dGTP, 400 nM primer T1 and 400 nM primer T2, 1.5 U Pfu DNA polymerase, 20 ng fragment T1QR and 20 ng fragment QFT2, and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-T299Q was separated on 1% agarose gel and recovered using QIAquick Gel Extraction Kit. Plasmid pGEMT-MGI-T299Q, generated after ligation of MGI-T299Q into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI-T299Q DNA was then isolated from the positive clones and sequenced.

Example 6

Generation of Glucose Isomerase Mutant MGI-4 Containing Four Mutations

The site directed mutagenesis was done as described by Ho et al., *Gene* 77:51-59, 1989 and White et al., *PCR protocol: current methods and applications*. Totowa, N.J.: Humana Press 1993.

Fragments T1FR and QFT2 were amplified and recovered in accordance with Examples 2 and 5, respectively. Fragment FFAR was amplified using primer pair 139FF (Table 1) and 182AR (Table 2) on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer 139FF and 400 nM primer 182AR, 1.5 U Pfu DNA polymerase, 20 ng pGEMT-TS, and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment FFAR, was separated on 1% agarose gel and recovered using QIAquick Gel Extraction Kit. Fragment AFSR was amplified using primers 182AF and 187SR (Table 1) at the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer 182AF and 400 nM primer 187SR, 1.5 U Pfu DNA polymerase, 20 ng pGEMT-TS and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and firmly 72° C., 5 min. The fragment AFSR was separated on 1% agarose gel and recovered using QIAquick Gel Extraction Kit. Fragment SFQR was amplified using primers 187SF and 299QR (Table 1) at the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer 187SF and 400 nM primer 299QR, 1.5 U Pfu DNA polymerase, 20 ng pGEMT-TS and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The fragment SFQR was separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer T1 and 400 nM primer T2, 1.5 U Pfu DNA polymerase, 20 ng fragment T1FR and 20 ng fragment FFAR, 20 ng fragment AFSR, 20 ng fragment SFQR and 20 ng fragment QFT2 and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-4 was separated on 1% agarose gel and recovered using QIAquick Gel Extraction Kit. Plasmid pGEMT-MGI-4, generated after ligation of MGI-4 into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI-4 DNA was then isolated from the positive clones and sequenced. The sequence of the MGI-4 contains four mutations including W139F, R182A, F187S and T299Q.

Example 7

Generation of Glucose Isomerase Mutants MGI4-F87L and MGI4-F87M Containing Five Mutations The site directed mutagenesis was done as described by Ho et al., *Gene* 77:51-59, 1989 and White et al., *PCR protocol: current methods and applications*. Totowa, N.J.: Humana Press 1993.

Using pGEMT-MGI-4 (Example 6) as template, the Phe (F) at position 87 of the MGI-4 was mutated to Leu (L), generating mutant MGI4-F87L by PCR amplification with site-directed primers 87LF and 87LR (Table 1) and universal primers T1 and T2 (Table 1).

Fragments T1LR and LFT2 were amplified by primer pairs of T1 and 87LR, and 87LF and T2 respectively on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer T1 and 400 nM primer 87LR or 400 nM primer 87LF and 400 nM primer T2, 1.5 U Pfu DNA polymerase (Promega, USA), 20 ng pGEMT-MGI-4, and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragments T1LR and LFT2, were separated on 1% agarose gel and recovered using QIAquick Gel Extraction Kit (QIAGEN, German). The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer T1 and 400 nM primer T2, 1.5 U Pfu DNA polymerase, 20 ng fragment T1LR and 20 ng fragment LFT2 and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI4-F87L was separated on 1% agarose gel and recovered using QIAquick Gel Extraction Kit. Plasmid pGEMT-MGI4-F87L, generated after ligation of MGI4-F87L into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-F87L DNA was then isolated from the positive clones and sequenced. MGI4-F87L sequence contains five mutations of F87L, W139F, R182A, F187S and T299Q. Amino acid sequence of MGI4-F87L is shown as Sequence 5 in the Sequence Listing.

MGI4-F87M was constructed using similar procedures. The primers used are shown in Table 1. The mutant MGI4-F87M contains five mutations of F87M, W139F, R182A, F187S and T299Q. Amino acid sequence of MGI4-F87M is shown as Sequence 6 in the Sequence Listing.

Example 8

Generation of Glucose Isomerase Mutants MGI4-V217R and MGI4-V217W Containing Five Mutations The site directed mutagenesis was done as described by Ho et al., *Gene* 77:51-59, 1989 and White et al., *PCR protocol: current methods and applications*. Totowa, N.J.: Humana Press 1993.

Using pGEMT-MGI-4 (Example 6) as template, the Val (V) at position 217 of the MGI-4 was mutated to Arg (R), generating mutant MGI4-V217R by PCR amplification with site-directed primers 217RF and 217RR (Table 1) and universal primers T1 and T2 (Table 1).

Fragments T1RR and RFT2 were amplified by primer pairs of T1 and 217RR, and 217RF and T2 respectively on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μL dTTP, 50 μM dCTP, 50 μM dGTP, 400 nM primer T1 and 400 nM primer 217RR or 400 nM primer 217RF and 400 nM primer T2, 1.5 U Pfu DNA polymerase, 20 ng pGEMT-MGI-4, and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragments T1RR and RFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer T1 and 400 nM primer T2, 1.5 U Pfu DNA polymerase, 20 ng fragment T1RR and 20 ng fragment RFT2 and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI4-V217R was separated on 1% agarose gel and recovered using QIAquick Gel Extraction Kit. Plasmid pGEMT-MGI4-V217R, generated after ligation of MGI4-V217R into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-V217R DNA was then isolated from the positive clones and sequenced. The sequence of the mutant contains five mutations of W139F, R182A, F187S, V217R and T299Q. Amino acid sequence of MGI4-V217R is shown as Sequence 7 in the Sequence Listing.

MGI4-V217W was constructed using similar procedures. The primers used are shown in Table 1. The mutant MGI4-V217W contains five mutations of W139F, R182A, F187S, V217W and T299Q. Amino acid sequence of MGI4-V217R is shown as Sequence 8 in the Sequence Listing.

Example 9

Generation of Glucose Isomerase Mutant MGI4-D260E Containing Five Mutations

The site directed mutagenesis was done as described by Ho et al., *Gene* 77:51-59, 1989 and White et al., *PCR protocol: current methods and applications*. Totowa, N.J.: Humana Press 1993.

Using pGFMT-MGI-4 (Example 6) as template, the Asp (D) at position 260 of the MGI-4 was mutated to Glu (E), generating mutant MGI4-D260E by PCR amplification with site-directed primers 260EF and 260ER (Table 1) and universal primers T1 and T2 (Table 1).

Fragments T1ER and EFT2 were amplified by primer pairs of T1 and 260ER, and 260EF and T2 respectively on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer T1 and 400 nM primer 260ER or 400 mM primer 260EF and 400 mM primer T2, 1.5 U Pfu DNA polymerase, 20 ng pGEMT-MGI-4, and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragments T1ER and EFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 mM primer T1 and 400 nM primer T2, 1.5 U Pfu DNA polymerase, 20 ng fragment T1ER and 20 ng fragment EFT2 and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI4-D260E was separated on 1% agarose gel and recovered using QIAquick Gel Extraction Kit. Plasmid pGEMT-MGI4-D260E, generated after ligation of MGI4-D260E into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-D260E DNA was then isolated from the positive clones and sequenced. The sequence of the mutant contains five mutations of W139F, R182A, F187S, D260E and T299Q. Amino acid sequence of MGI4-D260E is shown as Sequence 9 in the Sequence Listing.

Example 10

Generation of Glucose Isomerase Mutant MGI4-F276G Containing Five Mutations

The site directed mutagenesis was done as described by Ho et al., *Gene* 77:51-59, 1989 and White et al., *PCR protocol: current methods and applications*. Totowa, N.J.: Humana Press 1993.

Using pGEMT-MGI-4 (Example 6) as template, the Phe (F) at position 276 of the MGI-4 was mutated to Gly (G), generating mutant MGI4-F276G by PCR amplification with site-directed primers 276GF and 276GR (Table 1) and universal primers T1 and T2 (Table 1).

Fragments T1GR and GFT2 were amplified by primer pairs of T1 and 276GR, and 276GF and T2 respectively on the following condition: 20 mM Tris-HCl (pH 8.8), 10 mM KCl, 10 mM (NH$_4$)$_2$SO$_4$, 2 mM MgSO$_4$, 0.1% Triton X-100, 50 μM dATP, 50 μM dTTP, 50 μM dCTP, 50 μM dGTP, 400 nM primer T1 and 400 nM primer 276GR or 400 nM primer 276GF and 400 nM primer T2, 1.5 U Pfu DNA polymerase, 20 ng pGEMT-MGI-4, and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragments T1GR and GFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM (NH$_4$)$_2$SO$_4$, 2 mM MgSO$_4$, 0.1% Triton X-100, 50 μM dATP, 50 μM dTTP, 50 μM dCTP, 50 μM dGTP, 400 nM primer T1 and 400 nM primer T2, 1.5 U Pfu DNA polymerase, 20 ng fragment T1GR and 20 ng fragment GFT2 and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI4-F276G was separated on 1% agarose gel and recovered using QIAquick Gel Extraction Kit, Plasmid pGEMT-MGI4-F276G, generated after ligation of MGI4-F276G into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-F276G DNA was then isolated from the positive clones and sequenced. The sequence of the mutant contains five mutations of W139F, R182A, F187S, F276G and T299Q. Amino acid sequence of MGI4-F276G is shown as Sequence 10 in the Sequence Listing.

Example 11

Generation of Glucose Isomerase Mutants MGI4-24 and MGI4-25 Containing Six Mutations The site directed mutagenesis was done as described by Ho et al., *Gene* 77:51-59, 1989 and White et al., *PCR protocol: current methods and applications*. Totowa, N.J. Humana Press 1993.

Fragment T1LR was amplified and recovered as in Example 7. Fragment LFAR was amplified with primers pair 87LF and 260AR (Table 1) and recovered. The amplification condition was: 20 mM Tris-HCl (pH 8.8), 10 mM KCl, 10 mM (NH$_4$)$_2$SO$_4$, 2 mM MgSO$_4$, 0.1% Triton X-100, 50 μM dATP, 50 μM dTTP, 50 μM dCTP, 50 μM dGTP, 400 nM primer 87LF and 400 nM primer 260AR, 1.5 U Pfu DNA polymerase, 20 ng pGEMT-MGI-4, and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment LFAR, was separated on 1% agarose gel and recovered using QIAquick Gel Extraction Kit. Fragment AFT2 was amplified with primer pair of 260AF and T2 (Table 1) on the following condition: 20 mM Tris-HCl (pH 8.8), 10 mM KCl, 10 mM (NH$_4$)$_2$SO$_4$, 2 mM MgSO$_4$, 0.1% Triton X-100, 50 μM dATP, 50 μM dTTP, 50 μM dCTP, 50 μM dGTP, 400 nM primer 260AF and 400 nM primer T2, 1.5 U Pfu DNA polymerase, 20 ng pGEMT-MGI-4 and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The fragment AFT2 was separated on 1% agarose gel and recovered using QIAquick Gel Extraction Kit. The full length glucose isomerase gene was amplified at the following condition: 20 mM Tris-HCl (pH 8.8), 10 mM KCl, 10 mM (NH$_4$)$_2$ SO$_4$, 2 mM MgSO$_4$, 0.1% Triton X-100, 50 μM dATP, 50 μM dTTP, 50 μM dCTP, 50 μM dGTP, 400 nM primer T1 and 400 nM primer T2, 1.5 U Pfu DNA polymerase, 20 ng fragment T1LR, 20 ng fragment LFAR and 20 ng fragment AFT2, the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutated gene MGI4-24 was separated on 1% agarose gel and recovered using QIAquick Gel Extraction Kit. Plasmid pGEMT-MGI4-24, generated after ligation of MGI4-24 into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-24 DNA was then isolated from the positive clones and sequenced. Amino acid sequence of MGI4-24 is shown as Sequence 11 in the Sequence Listing. The sequence of the mutant contains six mutations of F87L, W139F, R182A, F187S, D260A and T299Q.

MGI4-25 was constructed using similar procedures. The primer pairs T1 and 87LR, 87LF and 276TR, 276TF and T2 used are shown in Table 1. The mutant contains six mutations of F87L, W139F, R182A, F187S, F276T and T299Q. Amino acid sequence of the mutant is shown as Sequence 12 in the Sequence Listing.

Example 12

Generation of Glucose Isomerase Mutants MGI4-34 and MGI4-35 Containing Seven Mutations The site directed mutagenesis was done as described by Ho et al., Gene 77:51-59, 1989 and White et al, *PCR protocol: current methods and applications*. Totowa, N.J.: Humana Press 1993.

Fragment T1LR was amplified and recovered as in Example 7. Fragment LFGR was amplified with primers pair 87LF and 217GR (Table 1) and recovered. The amplification condition was: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer 87LF and 400 nM primer 217GR, 1.5 U Pfu DNA polymerase, 20 ng pGEMT-MGI-4, and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment LFGR, was separated on 1% agarose gel and recovered using QIAquick Gel Extraction Kit. Amplification of fragment GFTR was carried out on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer 217GF and 400 nM primer 276TR, 1.5 U Pfu DNA polymerase, 20 ng pGEMT-MGI-4 and the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The fragment GFTR was separated on 1% agarose gel and recovered using QIAquick Gel Extraction Kit. Fragment TFT2 was amplified with primer pair 276TF an T2 (Table 1) on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer 276TF and 400 nM primer T2, 1.5 U Pfu DNA polymerase, 20 ng pGEMT-MGI-4, the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The fragment TFT2 was separated on 1% agarose gel and recovered using QIAquick Gel Extraction Kit. The full-length glucose isomerase gene was amplified on the following condition: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer T1 and 400 nM primer T2, 1.5 U Pfu DNA polymerase, 20 ng fragment T1LR, 20 ng fragment LFGR, 20 ng fragment GFTR and 20 ng fragment TFT2, the total volume was adjusted to 50 μl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutated gene MGI4-34 was separated on 1% agarose gel and recovered using QIAquick Gel Extraction Kit. Plasmid pGEMT-MGI4-34, generated after ligation of MGI4-34 into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-34 DNA was then isolated from the positive clones and sequenced. The sequence of the mutant contains seven mutations of F87L, W139F, R182A, F187S, V217G, F276T and T299Q. Amino acid sequence of MGI4-34 is shown as Sequence 13 in the Sequence Listing.

MGI4-35 was constructed using similar procedures. The primer pairs T1 and 87LR, 87LF and 217GR, 217GF and 260AR, 260AF and T2 used are shown in Table 1. The mutant contains seven mutations of F87L, W139F, R182A, F187S, V217G, D260A and T299Q. Amino acid sequence of the mutant is shown as Sequence 14 in the Sequence Listing.

TABLE 1

The Primers Used for Amplification of Wild-type Glucose Isomerase and the Mutants in Examples 1-12

| Product | | Primer Pair |
|---|---|---|
| Wild-type | T1: | 5'AGCCTAGGTTAATTAACTTTAAG AAGGAGATATACATATGAATAAATA TTTTGAGA 3' |
| | T2: | 5'ATAAGCTCAGCGGCGCGCCTTAT TCTGCAAACAAATAC 3' |
| Mutant MGI-W139F | 139FF: | 5'AAAAGTTTTGTTTGGTACCGCAA ATCTTTTCTC 3' |
| | 139FR: | 5'TTGCGGTACCAAACAAAACTTTT GTCTTGCTGG 3' |
| Mutant MGI-R182A | 182AF: | 5'GGAGCTTGGCGCGGAAAACTACG TATTTTGGGG 3' |
| | 182AR: | 5'CGTAGTTTTCCGCGCCAAGCTCC TTAGTAATCT 3' |
| Mutant MGI-F187S | 187SF: | 5'ACTACGTAAGCTGGGGTGGAAGA GAAGGGT 3' |
| | 187SR: | 5'CCACCCCAGCTTACGTAGTTTTC GCGGCCA 3' |
| Mutant MGI-T299Q | 299QF: | 5'TGACGCAAATCAAGGCGACATGC TTTTGGGATG 3' |
| | 299QR: | 5'GCATGTCGCCTTGATTTGCGTCG ATTGATCCTA 3' |
| Mutant MGI4-F87L | 87LF: | 5'GAAGCAGCACTGGAGTTTTTTGA TAAGATAA 3' |
| | 87LR: | 5'AAAAACTCCAGTGCTGCTTCTAC CCTTGCTTTC 3' |
| Mutant MGI4-F87M | 87MF: | 5'GAAGCAGCAATGGAGTTTTTTGA TAAGATAA 3' |
| | 87MR: | 5'AAAAACTCCATTGCTGCTTCTAC CCTTGCTTTC 3' |
| Mutant MGI4-V217G | 217GF: | 5'ACATGGCTGGCGACTATGCAAAG GAAATCG 3' |
| | 217GR: | 5'GCATAGTCGCCAGCCATGTGCAA AAATCTT 3' |
| Mutant MGI4-V217W | 217WF: | 5'ACATGGCTTGGGACTATGCAAAG GAAATCG 3' |
| | 217WR: | 5'GCATAGTCCCAAGCCATGTGCAA AAATCTT 3' |
| Mutant MGI4-V217T | 217TF: | 5'ACATGGCTACCGACTATGCAAAG GAAATCG 3' |
| | 217TR: | 5'GCATAGTCGGTAGCCATGTGCAA AAATCTT 3' |
| Mutant MGI4-D260E | 260EF: | 5'ACGACCTTGAAAAATATTTCAAA GTAAATA 3' |
| | 260ER: | 5'AAATATTTTTCAAGGTCGTATTT TCTCAAG 3' |

TABLE 1-continued

The Primers Used for Amplification of Wild-type Glucose Isomerase and the Mutants in Examples 1-12

| Product | Primer Pair | |
|---|---|---|
| Mutant MGI4-D260A | 260AF: | 5'ACGACCTTGCGAAATATTTCAAA GTAAATA 3' |
| | 260AR: | 5'AAATATTTCGCAAGGTCGTATTT TCTCAAG 3' |
| Mutant MGI4-F276G | 276GF: | 5'ACATTGGCAGGCCACGACTTCCA ACATGAGC 3' |
| | 276GR: | 5'GAAGTCGTGGCCTGCCAATGTCG CATGGTTT3' |
| Mutant MGI4-F276T | 276TF: | 5'ACATTGGCAACCCACGACTTCCA ACATGAGC 3' |
| | 276TR: | 5'GAAGTCGTGGGTTGCCAATGTCG CATGGTTT 3' |

Example 13

Isolation and Purification of Wild-Type Glucose Isomerase

The isolation and purification of wild-type glucose isomerase were carried out in accordance with Lee et al., *Journal of General Microbiology*, 139:1227-1234, 1993.

Plasmid pGEMT-TS transformed *E. coli* HB101 cells were incubated on MacConkey plate containing 1% D-xylose and 50 mg/L ampicillin at 37° C. for 36 hours. A single colony from the plate was inoculated and cultivated in 5 ml LB supplemented with 50 mg/L ampicillin for 16 hours. The bacterial cells were pelleted, resuspended in 1 ml 20 nM sodium phosphate buffer (pH 6.5), added $CoCl_2$ and $MgCl_2$ to final concentrations of 250 µM and 5 mM respectively, disrupted using ultrasonication and centrifuged at 17,800 g for 15 min at 10° C. to collect the supernatant as crude protein. The crude protein was heated at 80° C. for 10 min and centrifuged at 17,800 g for 15 min at 10° C. to remove the precipitate. The resultant partially purified glucose isomerase was used in the subsequent assays and for preparation of high fructose corn syrup.

Example 14

Isolation and Purification of Glucose Isomerase Mutants

The isolation and purification of glucose isomerase mutant MGI4-35 were carried out as described in Example 13, except the plasmid used was pGEMT-MGI4-35. Other glucose isomerase mutants were also isolated and purified as described in Example 13.

Example 15

Activity Assay of Wild-Type Glucose Isomerase with D-Glucose as Substrate

Stock substrate solution A containing 1.0 M D-glucose, 20 mM sodium phosphate buffer, 250 µM $CoCl_2$ and 5 mM $MgCl_2$, pH 6.5 was prepared, Ninety µl of the stock substrate solution A were mixed with 10 µl of the glucose isomerase prepared as described in Examples 1 and 13, incubated at 80° C. for 10 min and quenched on ice immediately. The D-fructose formed was measured by the cysteine-carbazole method (Dische et al., *Journal of Biological Chemistry*, 192:583-587, 1951; and Nakamura, *Agricultural and Biological Chemistry*, 32:701-706, 1968). Protein concentration was determined using Coomassie® Plus Protein Assay Reagent Kit (Pierce, USA) and SDS-PAGE. One unit of enzyme activity is defined as the amount of enzyme that is used to produce 1 µmole of fructose from D-glucose per min under the assay condition. Table 2 below shows the relative specific activity of wild-type glucose isomerase.

Example 16

Activity Assay of Glucose Isomerase Mutants

The activity of glucose isomerase mutant was measured as described in Example 15. Table 2 below shows the comparison of the relative specific activities of wild-type glucose isomerase and the mutants.

TABLE 2

The Specific Activities of Wild-type Glucose Isomerase and the Mutants

| Enzyme | SEQ ID NO. of the Amino Acid Sequence | Relative Specific Activity |
|---|---|---|
| Wild-type | SEQ ID NO.: 2 | 100 |
| MGI4-F87L | SEQ ID NO.: 5 | 271 |
| MGI4-F87M | SEQ ID NO.: 6 | 346 |
| MGI4-V217R | SEQ ID NO.: 7 | 609 |
| MGI4-V217W | SEQ ID NO.: 8 | 151 |
| MGI4-D260E | SEQ ID NO.: 9 | 560 |
| MGI4-F276G | SEQ ID NO.: 10 | 365 |
| MGI4-24 | SEQ ID NO.: 11 | 501 |
| MGI4-25 | SEQ ID NO.: 12 | 652 |
| MGI4-34 | SEQ ID NO.: 13 | 869 |
| MGI4-35 | SEQ ID NO.: 14 | 827 |

Example 17

Thermostability of Wild-Type Glucose Isomerase

Two hundred µl of the partially purified wild-type glucose isomerase obtained as described in Example 13 were added to each of four microfuge tubes, and overlaid with 200 µl mineral oil. The tubes were placed in an 80° C. water bath. One of the four tubes was removed from the water bath at a time interval of 0 h, 2 h, 6 h and 27 h, and centrifuged at 17,800 g for 20 min at 10° C. The residual protein and the glucose isomerase activity of the supernatants were determined as described in Example 15. FIG. 1 shows the thermostability of wild-type glucose isomerase at 80° C.

Example 18

Thermostability of Glucose Isomerase Mutants

The thermostability of glucose isomerase mutants MGI4-34 or MGI4-35 (see Examples 12 and 14) was measured as described in Example 17 and was shown in FIG. 1. As shown in FIG. 1, the half-life of the activity of wild-type glucose isomerase at 80° C. was 4.1 hours, that of MGI4-34 was 26 hours and that of MGI4-35 was greater than 27 hours.

Example 19

Immobilization of Glucose Isomerase Mutant MGI4-35

The immobilization procedure was carried out in accordance with Ge et al., Applied Biochemistry and Biotechnology, 69:17-29, 1998. Briefly, 100 g of immobilization carrier (ethylamine polystyrene hydrochloride particles, provided by Chengdu Institute of Chemical Engineering), were mixed with 8 g of the partially purified glucose isomerase mutant MGI4-35 prepared as described in Examples 12 and 14 in 1 L of 10 mM phosphate buffer (pH 8.0) and stirred (60-120 rpm/mm) at room temperature (22.degree. C.) for 18 hours. The resultant immobilized enzyme was collected by filtration and washed with water three times to obtain 107 g immobilized enzyme. The activity of the immobilized enzyme measured as described in Example 16 using 0.01 g of the immobilized enzyme, was 820 units/g.

Example 20

Immobilization of E. coli Cells Carrying Glucose Isomerase Mutant MGI4-35

E. coli HB101 cells carrying pGEMT-MGI4-35 were grown in LB broth containing 50 mg/L ampicillin to $OD_{600}$ of 7. Ten g of the cells, collected by centrifugation, were mixed well with 20 g of 3% sodium alginate, squeezed through a needle of 0.5 mm in diameter into 500 ml of 2% $CaCl_2$ solution. The mixture was allowed to react for 1 hour at room temperature and washed three times by soaking in distilled water for half an hour each. The resultant immobilized cells of approximate 30 g were measured for glucose isomerase activity as described in Example 16 using 0.01 g of the immobilized cells. The activity was 370 units/g.

This invention is not limited by the detailed description in the Examples above. Various modifications can be made by those skilled in the art without departing from the scope of the invention.

The invention claimed is:

1. An isolated glucose isomerase mutant comprising the amino acid sequence of SEQ ID NO: 2, wherein the amino acid at position 139 is mutated to phenylalanine (Phe), the amino acid at position 182 is mutated to alanine (Ala), the amino acid at position 187 is mutated to serine (Ser), the amino acid at position 299 is mutated to glutamine (Gln) and the glucose isomerase mutant has at least one mutation at position 87, position 217, position 260, or position 276, and the glucose isomerase mutant has a higher catalytic activity than that of a wild-type glucose isomerase when using D-glucose as substrate.

2. The glucose isomerase mutant according to claim 1, wherein, the amino acid at position 87 is mutated to methionine (Met) or leucine (Leu).

3. The glucose isomerase mutant according to claim 1, wherein, the amino acid at position 217 is mutated to arginine (Arg), tryptophan (Trp) or glycine (Gly).

4. The glucose isomerase mutant according to claim 1, wherein, the amino acid at position 260 is mutated to glutamic acid (Glu) or alanine (Ala).

5. The glucose isomerase mutant according to claim 1, wherein, the amino acid at position 276 is glycine (Gly) or threonine (Thr).

6. The glucose isomerase mutant according to claim 1, wherein, the glucose isomerase mutant further comprises any one of the amino acid sequences of SEQ ID NO: 5 to SEQ ID NO: 14.

* * * * *

SEQUENCE LISTING

<160> NUMBER OF SEQ ID NOS: 14

<210> SEQ ID NO 1
<211> LENGTH: 1320
<212> TYPE: DNA
<213> ORGANISM: Thermoanaerobacterium saccharolyticum

<400> SEQUENCE: 1

```
atgaataaat attttgagaa cgtatctaaa ataaaatatg aaggaccaaa atcaaataat      60
ccttattcct ttaaatttta caatccagag gaagtaatcg atggcaagac gatggaggag     120
catctccgct tttctatagc ttattggcac acttttactg ctgatggaac agatcaattt     180
ggcaaggcta ctatgcaaag accatggaac cactacacag atcctatgga tatagcgaaa     240
gcaagggtag aagcagcatt tgagtttttt gataagataa atgcaccttt cttctgcttc     300
catgataggg atattgcccc tgaaggagat actcttagag agacaaacaa aaacttagat     360
acaatagttg ctatgataaa ggattactta aagaccagca agacaaaagt tttgtggggt     420
accgcaaatc tttctccaa tccgagattt gtacatggtg catcaacatc ctgcaatgct     480 gacgttttg catattctgc agcgcaagtc aaaaaagccc ttgagattac taaggagctt     540
ggccgcgaaa actacgtatt ttggggtgga agagaagggt acgagacgct tctcaataca     600
gatatggagt tagagcttga taactttgca agattttttgc acatggctgt tgactatgca     660
aaggaaatcg gctttgaagg tcagttcttg attgagccga agccaaagga gcctacaaaa     720
catcaatacg actttgacgt ggcaaatgta ttggcattct tgagaaaata cgaccttgac     780
aaatatttca aagtaaatat cgaagcaaac catgcgacat tggcattcca cgacttccaa     840
catgagctaa gatacgccag aataaacggt gtattaggat caattgacgc aaatacaggc     900
gacatgcttt tgggatggga tacggaccag ttccctacag atatacgcat gacaacgctt     960
gctatgtatg aagtcataaa gatgggtgga tttgacaaag gtggccttaa ctttgatgca    1020
aaagtaagac gtgcttcatt tgagccagaa gatcttttct taggtcacat agcaggaatg    1080
gatgcttttg caaaaggctt taagttgct tacaagcttg tgaaagatgg cgtatttgac    1140
aagttcatcg aagaaagata cgcaagctac aaagaaggca ttggcgctga tattgtaagc    1200
```

```
ggtaaagctg acttcaagag ccttgaaaag tatgcattag agcacagcca gattgtaaac   1260
aaatcaggca gacaagagct attagaatca atcctaaatc agtatttgtt tgcagaataa   1320
```

<210> SEQ ID NO 2
<211> LENGTH: 439
<212> TYPE: PRT
<213> ORGANISM: Thermoanaerobacterium saccharolyticum

<400> SEQUENCE: 2

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350
```

-continued

```
Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 3
<211> LENGTH: 1320
<212> TYPE: DNA
<213> ORGANISM: Thermoanaerobacterium saccharolyticum
<220> FEATURE:
<221> NAME/KEY: misc_feature
<222> LOCATION: (259)..(261)
<223> OTHER INFORMATION: "n" represents a,t,g or c; and "nnn" represents
      any amino acid code except for phenylalanine.
<220> FEATURE:
<221> NAME/KEY: misc_feature
<222> LOCATION: (649)..(651)
<223> OTHER INFORMATION: "n" represents a,t,g or c; and "nnn" represents
      any amino acid code except for Valine.
<220> FEATURE:
<221> NAME/KEY: misc_feature
<222> LOCATION: (778)..(780)
<223> OTHER INFORMATION: "n" represents a,t,g or c; and "nnn" represents
      any amino acid code except for aspartic acid.
<220> FEATURE:
<221> NAME/KEY: misc_feature
<222> LOCATION: (826)..(828)
<223> OTHER INFORMATION: "n" represents a,t,g or c; and "nnn" represents
      any amino acid code except for phenylalanine.

<400> SEQUENCE: 3
atgaataaat attttgagaa cgtatctaaa ataaaatatg aaggaccaaa atcaaataat      60
ccttattcct ttaaatttta caatccagag gaagtaatcg atggcaagac gatggaggag     120
catctccgct tttctatagc ttattggcac acttttactg ctgatggaac agatcaattt     180
ggcaaggcta ctatgcaaag accatggaac cactacacag atcctatgga tatagcgaaa     240
gcaagggtag aagcagcann ngagtttttt gataagataa atgcaccttt cttctgcttc     300
catgataggg atattgcccc tgaaggagat actcttagag agacaaacaa aaacttagat     360
acaatagttg ctatgataaa ggattactta aagaccagca agacaaaagt tttgtggggt     420
accgcaaatc ttttctccaa tccgagattt gtacatggtg catcaacatc ctgcaatgct     480 gacgttttg catattctgc agcgcaagtc aaaaagccc ttgagattac taaggagctt     540
ggccgcgaaa actacgtatt tggggtggaa agagaagggt acgagacgct tctcaataca     600
gatatggagt tagagcttga taactttgca agatttttgc acatggctnn ngactatgca     660
aaggaaatcg gctttgaagg tcagttcttg attgagccga agccaaagga gcctacaaaa     720
catcaatacg actttgacgt ggcaaatgta ttggcattct tgagaaaata cgaccttnnn     780
aaatatttca agtaaatat cgaagcaaac catgcgacat ggcannnca cgacttccaa     840 catgagctaa gatacgccag aataaacggt gtattaggat caattgacgc aaatacaggc     900
gacatgcttt tgggatggga tacgaccag ttccctacag atatacgcat gacaacgctt     960
gctatgtatg aagtcataaa gatgggtgga tttgacaaag gtggccttaa ctttgatgca    1020
```

-continued

```
aaagtaagac gtgcttcatt tgagccagaa gatcttttct taggtcacat agcaggaatg    1080
gatgcttttg caaaaggctt taaagttgct tacaagcttg tgaaagatgg cgtatttgac    1140
aagttcatcg aagaaagata cgcaagctac aaagaaggca ttggcgctga tattgtaagc    1200
ggtaaagctg acttcaagag ccttgaaaag tatgcattag agcacagcca gattgtaaac    1260
aaatcaggca gacaagagct attagaatca atcctaaatc agtatttgtt tgcagaataa    1320
```

<210> SEQ ID NO 4
<211> LENGTH: 439
<212> TYPE: PRT
<213> ORGANISM: Thermoanaerobacterium saccharolyticum
<220> FEATURE:
<221> NAME/KEY: MISC_FEATURE
<222> LOCATION: (87)..(87)
<223> OTHER INFORMATION: Xaa represents any amino acid residue other than phenylalanine.
<220> FEATURE:
<221> NAME/KEY: MISC_FEATURE
<222> LOCATION: (217)..(217)
<223> OTHER INFORMATION: Xaa represents any amino acid residue other than Valine.
<220> FEATURE:
<221> NAME/KEY: MISC_FEATURE
<222> LOCATION: (260)..(260)
<223> OTHER INFORMATION: Xaa represents any amino acid residue other than aspartic acid.
<220> FEATURE:
<221> NAME/KEY: MISC_FEATURE
<222> LOCATION: (276)..(276)
<223> OTHER INFORMATION: Xaa represents any amino acid residue other than phenylalanine.

<400> SEQUENCE: 4

```
Met Asn Lys Tyr Phe Glu Asn Val Ser Lys Ile Lys Tyr Glu Gly Pro
 1               5                  10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Xaa Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Xaa Asp Tyr Ala Lys Glu Ile Gly
```

```
            210                 215                 220
Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Xaa Lys Tyr Phe Lys Val Asn Ile Glu Ala Asn His Ala
            260                 265                 270

Thr Leu Ala Xaa His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 5
<211> LENGTH: 439
<212> TYPE: PRT
<213> ORGANISM: Thermoanaerobacterium saccharolyticum

<400> SEQUENCE: 5

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140
```

```
Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 6
<211> LENGTH: 439
<212> TYPE: PRT
<213> ORGANISM: Thermoanaerobacterium saccharolyticum

<400> SEQUENCE: 6

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80
```

```
Ala Arg Val Glu Ala Ala Met Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 7
<211> LENGTH: 439
<212> TYPE: PRT
<213> ORGANISM: Thermoanaerobacterium saccharolyticum

<400> SEQUENCE: 7

Met Asn Lys Tyr Phe Glu Asn Val Ser Lys Ile Lys Tyr Glu Gly Pro
```

```
1               5                   10                  15
Lys Ser Asn Asn Pro Tyr Ser Phe Lys Phe Tyr Asn Pro Glu Glu Val
                    20                  25                  30

Ile Asp Gly Lys Thr Met Glu Glu His Leu Arg Phe Ser Ile Ala Tyr
                    35                  40                  45

Trp His Thr Phe Thr Ala Asp Gly Thr Asp Gln Phe Gly Lys Ala Thr
                    50                  55                  60

Met Gln Arg Pro Trp Asn His Tyr Thr Asp Pro Met Asp Ile Ala Lys
 65                     70                  75                  80

Ala Arg Val Glu Ala Ala Phe Glu Phe Asp Lys Ile Asn Ala Pro
                    85                  90                  95

Phe Phe Cys Phe His Asp Arg Asp Ile Ala Pro Glu Gly Asp Thr Leu
                    100                 105                 110

Arg Glu Thr Asn Lys Asn Leu Asp Thr Ile Val Ala Met Ile Lys Asp
                    115                 120                 125

Tyr Leu Lys Thr Ser Lys Thr Lys Val Leu Phe Gly Thr Ala Asn Leu
                    130                 135                 140

Phe Ser Asn Pro Arg Phe Val His Gly Ala Ser Thr Ser Cys Asn Ala
145                     150                 155                 160

Asp Val Phe Ala Tyr Ser Ala Ala Gln Val Lys Lys Ala Leu Glu Ile
                    165                 170                 175

Thr Lys Glu Leu Gly Ala Glu Asn Tyr Val Ser Trp Gly Gly Arg Glu
                    180                 185                 190

Gly Tyr Glu Thr Leu Leu Asn Thr Asp Met Glu Leu Glu Leu Asp Asn
                    195                 200                 205

Phe Ala Arg Phe Leu His Met Ala Arg Asp Tyr Ala Lys Glu Ile Gly
                    210                 215                 220

Phe Glu Gly Gln Phe Leu Ile Glu Pro Lys Pro Lys Glu Pro Thr Lys
225                     230                 235                 240

His Gln Tyr Asp Phe Asp Val Ala Asn Val Leu Ala Phe Leu Arg Lys
                    245                 250                 255

Tyr Asp Leu Asp Lys Tyr Phe Lys Val Asn Ile Glu Ala Asn His Ala
                    260                 265                 270

Thr Leu Ala Phe His Asp Phe Gln His Glu Leu Arg Tyr Ala Arg Ile
                    275                 280                 285

Asn Gly Val Leu Gly Ser Ile Asp Ala Asn Gln Gly Asp Met Leu Leu
                    290                 295                 300

Gly Trp Asp Thr Asp Gln Phe Pro Thr Asp Ile Arg Met Thr Thr Leu
305                     310                 315                 320

Ala Met Tyr Glu Val Ile Lys Met Gly Gly Phe Asp Lys Gly Gly Leu
                    325                 330                 335

Asn Phe Asp Ala Lys Val Arg Arg Ala Ser Phe Glu Pro Glu Asp Leu
                    340                 345                 350

Phe Leu Gly His Ile Ala Gly Met Asp Ala Phe Ala Lys Gly Phe Lys
                    355                 360                 365

Val Ala Tyr Lys Leu Val Lys Asp Gly Val Phe Asp Lys Phe Ile Glu
                    370                 375                 380

Glu Arg Tyr Ala Ser Tyr Lys Glu Gly Ile Gly Ala Asp Ile Val Ser
385                     390                 395                 400

Gly Lys Ala Asp Phe Lys Ser Leu Glu Lys Tyr Ala Leu Glu His Ser
                    405                 410                 415

Gln Ile Val Asn Lys Ser Gly Arg Gln Glu Leu Leu Glu Ser Ile Leu
                    420                 425                 430
```

Asn Gln Tyr Leu Phe Ala Glu
        435

<210> SEQ ID NO 8
<211> LENGTH: 439
<212> TYPE: PRT
<213> ORGANISM: Thermoanaerobacterium saccharolyticum

<400> SEQUENCE: 8

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Trp Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys

```
                355                 360                 365
Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 9
<211> LENGTH: 439
<212> TYPE: PRT
<213> ORGANISM: Thermoanaerobacterium saccharolyticum

<400> SEQUENCE: 9

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Glu Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285
```

```
Asn Gly Val Leu Gly Ser Ile Asp Ala Asn Gln Gly Asp Met Leu Leu
    290                 295                 300
Gly Trp Asp Thr Asp Gln Phe Pro Thr Asp Ile Arg Met Thr Thr Leu
305                 310                 315                 320
Ala Met Tyr Glu Val Ile Lys Met Gly Gly Phe Asp Lys Gly Gly Leu
                325                 330                 335
Asn Phe Asp Ala Lys Val Arg Arg Ala Ser Phe Glu Pro Glu Asp Leu
            340                 345                 350
Phe Leu Gly His Ile Ala Gly Met Asp Ala Phe Ala Lys Gly Phe Lys
        355                 360                 365
Val Ala Tyr Lys Leu Val Lys Asp Gly Val Phe Asp Lys Phe Ile Glu
    370                 375                 380
Glu Arg Tyr Ala Ser Tyr Lys Glu Gly Ile Gly Ala Asp Ile Val Ser
385                 390                 395                 400
Gly Lys Ala Asp Phe Lys Ser Leu Glu Lys Tyr Ala Leu Glu His Ser
                405                 410                 415
Gln Ile Val Asn Lys Ser Gly Arg Gln Glu Leu Leu Glu Ser Ile Leu
            420                 425                 430
Asn Gln Tyr Leu Phe Ala Glu
        435

<210> SEQ ID NO 10
<211> LENGTH: 439
<212> TYPE: PRT
<213> ORGANISM: Thermoanaerobacterium saccharolyticum

<400> SEQUENCE: 10

Met Asn Lys Tyr Phe Glu Asn Val Ser Lys Ile Lys Tyr Glu Gly Pro
1               5                   10                  15
Lys Ser Asn Asn Pro Tyr Ser Phe Lys Phe Tyr Asn Pro Glu Glu Val
            20                  25                  30
Ile Asp Gly Lys Thr Met Glu Glu His Leu Arg Phe Ser Ile Ala Tyr
        35                  40                  45
Trp His Thr Phe Thr Ala Asp Gly Thr Asp Gln Phe Gly Lys Ala Thr
    50                  55                  60
Met Gln Arg Pro Trp Asn His Tyr Thr Asp Pro Met Asp Ile Ala Lys
65                  70                  75                  80
Ala Arg Val Glu Ala Ala Phe Glu Phe Phe Asp Lys Ile Asn Ala Pro
                85                  90                  95
Phe Phe Cys Phe His Asp Arg Asp Ile Ala Pro Glu Gly Asp Thr Leu
            100                 105                 110
Arg Glu Thr Asn Lys Asn Leu Asp Thr Ile Val Ala Met Ile Lys Asp
        115                 120                 125
Tyr Leu Lys Thr Ser Lys Thr Lys Val Leu Phe Gly Thr Ala Asn Leu
    130                 135                 140
Phe Ser Asn Pro Arg Phe Val His Gly Ala Ser Thr Ser Cys Asn Ala
145                 150                 155                 160
Asp Val Phe Ala Tyr Ser Ala Ala Gln Val Lys Lys Ala Leu Glu Ile
                165                 170                 175
Thr Lys Glu Leu Gly Ala Glu Asn Tyr Val Ser Trp Gly Gly Arg Glu
            180                 185                 190
Gly Tyr Glu Thr Leu Leu Asn Thr Asp Met Glu Leu Glu Leu Asp Asn
        195                 200                 205
Phe Ala Arg Phe Leu His Met Ala Val Asp Tyr Ala Lys Glu Ile Gly
    210                 215                 220
```

-continued

```
Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
        260                 265                 270

Thr Leu Ala Gly His Asp Phe Gln His Glu Leu Arg Tyr Ala Arg Ile
            275                 280                 285

Asn Gly Val Leu Gly Ser Ile Asp Ala Asn Gln Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 11
<211> LENGTH: 439
<212> TYPE: PRT
<213> ORGANISM: Thermoanaerobacterium saccharolyticum

<400> SEQUENCE: 11

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
```

```
                145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
                180                 185                 190

Gly Tyr Glu Thr Leu Leu Asn Thr Asp Met Glu Leu Glu Leu Asp Asn
                195                 200                 205

Phe Ala Arg Phe Leu His Met Ala Val Asp Tyr Ala Lys Glu Ile Gly
                210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Ala Lys Tyr Phe Lys Val Asn Ile Glu Ala Asn His Ala
                260                 265                 270

Thr Leu Ala Phe His Asp Phe Gln His Glu Leu Arg Tyr Ala Arg Ile
                275                 280                 285

Asn Gly Val Leu Gly Ser Ile Asp Ala Asn Gln Gly Asp Met Leu Leu
                290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Leu
                325                 330                 335

Asn Phe Asp Ala Lys Val Arg Arg Ala Ser Phe Glu Pro Glu Asp Leu
                340                 345                 350

Phe Leu Gly His Ile Ala Gly Met Asp Ala Phe Ala Lys Gly Phe Lys
                355                 360                 365

Val Ala Tyr Lys Leu Val Lys Asp Gly Val Phe Asp Lys Phe Ile Glu
                370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430

Asn Gln Tyr Leu Phe Ala Glu
                435

<210> SEQ ID NO 12
<211> LENGTH: 439
<212> TYPE: PRT
<213> ORGANISM: Thermoanaerobacterium saccharolyticum

<400> SEQUENCE: 12

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
                35                  40                  45

Trp His Thr Phe Thr Ala Asp Gly Thr Asp Gln Phe Gly Lys Ala Thr
                50                  55                  60

Met Gln Arg Pro Trp Asn His Tyr Thr Asp Pro Met Asp Ile Ala Lys
65                  70                  75                  80
```

```
Ala Arg Val Glu Ala Ala Leu Glu Phe Phe Asp Lys Ile Asn Ala Pro
            85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
            130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Thr His Asp Phe Gln His Glu Leu Arg Tyr Ala Arg Ile
            275                 280                 285

Asn Gly Val Leu Gly Ser Ile Asp Ala Asn Gln Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 13
<211> LENGTH: 439
<212> TYPE: PRT
<213> ORGANISM: Thermoanaerobacterium saccharolyticum

<400> SEQUENCE: 13

Met Asn Lys Tyr Phe Glu Asn Val Ser Lys Ile Lys Tyr Glu Gly Pro
1               5                   10                  15
```

-continued

```
Lys Ser Asn Asn Pro Tyr Ser Phe Lys Phe Tyr Asn Pro Glu Glu Val
                 20                  25                  30
Ile Asp Gly Lys Thr Met Glu Glu His Leu Arg Phe Ser Ile Ala Tyr
             35                  40                  45
Trp His Thr Phe Thr Ala Asp Gly Thr Asp Gln Phe Gly Lys Ala Thr
         50                  55                  60
Met Gln Arg Pro Trp Asn His Tyr Thr Asp Pro Met Asp Ile Ala Lys
 65                  70                  75                  80
Ala Arg Val Glu Ala Ala Leu Glu Phe Phe Asp Lys Ile Asn Ala Pro
                 85                  90                  95
Phe Phe Cys Phe His Asp Arg Asp Ile Ala Pro Glu Gly Asp Thr Leu
            100                 105                 110
Arg Glu Thr Asn Lys Asn Leu Asp Thr Ile Val Ala Met Ile Lys Asp
            115                 120                 125
Tyr Leu Lys Thr Ser Lys Thr Lys Val Leu Phe Gly Thr Ala Asn Leu
        130                 135                 140
Phe Ser Asn Pro Arg Phe Val His Gly Ala Ser Thr Ser Cys Asn Ala
145                 150                 155                 160
Asp Val Phe Ala Tyr Ser Ala Ala Gln Val Lys Lys Ala Leu Glu Ile
                165                 170                 175
Thr Lys Glu Leu Gly Ala Glu Asn Tyr Val Ser Trp Gly Gly Arg Glu
            180                 185                 190
Gly Tyr Glu Thr Leu Leu Asn Thr Asp Met Glu Leu Glu Leu Asp Asn
        195                 200                 205
Phe Ala Arg Phe Leu His Met Ala Gly Asp Tyr Ala Lys Glu Ile Gly
    210                 215                 220
Phe Glu Gly Gln Phe Leu Ile Glu Pro Lys Pro Lys Glu Pro Thr Lys
225                 230                 235                 240
His Gln Tyr Asp Phe Asp Val Ala Asn Val Leu Ala Phe Leu Arg Lys
                245                 250                 255
Tyr Asp Leu Asp Lys Tyr Phe Lys Val Asn Ile Glu Ala Asn His Ala
            260                 265                 270
Thr Leu Ala Thr His Asp Phe Gln His Glu Leu Arg Tyr Ala Arg Ile
        275                 280                 285
Asn Gly Val Leu Gly Ser Ile Asp Ala Asn Gln Gly Asp Met Leu Leu
    290                 295                 300
Gly Trp Asp Thr Asp Gln Phe Pro Thr Asp Ile Arg Met Thr Thr Leu
305                 310                 315                 320
Ala Met Tyr Glu Val Ile Lys Met Gly Gly Phe Asp Lys Gly Gly Leu
                325                 330                 335
Asn Phe Asp Ala Lys Val Arg Arg Ala Ser Phe Glu Pro Glu Asp Leu
            340                 345                 350
Phe Leu Gly His Ile Ala Gly Met Asp Ala Phe Ala Lys Gly Phe Lys
        355                 360                 365
Val Ala Tyr Lys Leu Val Lys Asp Gly Val Phe Asp Lys Phe Ile Glu
    370                 375                 380
Glu Arg Tyr Ala Ser Tyr Lys Glu Gly Ile Gly Ala Asp Ile Val Ser
385                 390                 395                 400
Gly Lys Ala Asp Phe Lys Ser Leu Glu Lys Tyr Ala Leu Glu His Ser
                405                 410                 415
Gln Ile Val Asn Lys Ser Gly Arg Gln Glu Leu Leu Glu Ser Ile Leu
            420                 425                 430
```

Asn Gln Tyr Leu Phe Ala Glu
        435

<210> SEQ ID NO 14
<211> LENGTH: 439
<212> TYPE: PRT
<213> ORGANISM: Thermoanaerobacterium saccharolyticum

<400> SEQUENCE: 14

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Gly Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Ala Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

-continued

```
Val Ala Tyr Lys Leu Val Lys Asp Gly Val Phe Asp Lys Phe Ile Glu
        370             375             380
Glu Arg Tyr Ala Ser Tyr Lys Glu Gly Ile Gly Ala Asp Ile Val Ser
385                 390             395                 400
Gly Lys Ala Asp Phe Lys Ser Leu Glu Lys Tyr Ala Leu Glu His Ser
                405             410             415
Gln Ile Val Asn Lys Ser Gly Arg Gln Glu Leu Leu Glu Ser Ile Leu
            420             425             430
Asn Gln Tyr Leu Phe Ala Glu
        435
```